United States Patent
Cuckler et al.

(10) Patent No.: US 8,246,626 B2
(45) Date of Patent: Aug. 21, 2012

(54) METHOD FOR PERFORMING BONE CUTTING

(75) Inventors: John M. Cuckler, Birmingham, AL (US); Robert Metzger, Wakarusa, IN (US); Kurt Schmidt, Warsaw, IN (US); Trevor S. Schlueter, Gainesville, FL (US); James M. McKale, Leesburg, IN (US); Radu Serban, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 282 days.

(21) Appl. No.: 12/719,344

(22) Filed: Mar. 8, 2010

(65) Prior Publication Data
US 2010/0160918 A1 Jun. 24, 2010

Related U.S. Application Data

(60) Division of application No. 11/265,221, filed on Nov. 1, 2005, now Pat. No. 7,674,268, which is a continuation-in-part of application No. 10/680,902, filed on Oct. 8, 2003, now Pat. No. 7,364,580.

(51) Int. Cl.
*A61B 17/56* (2006.01)

(52) U.S. Cl. ........................................................ 606/88

(58) Field of Classification Search .............. 606/82–85, 606/86 R–89

See application file for complete search history.

(56) References Cited

U.S. PATENT DOCUMENTS

| | | | |
|---|---|---|---|
| 4,892,093 A * | 1/1990 | Zarnowski et al. | 606/82 |
| 5,047,032 A | 9/1991 | Jellicoe | |
| 5,047,033 A | 9/1991 | Fallin | |
| 5,304,181 A | 4/1994 | Caspari et al. | |
| 5,342,367 A * | 8/1994 | Ferrante et al. | 606/86 R |
| 5,405,349 A | 4/1995 | Burkinshaw et al. | |
| 5,415,662 A | 5/1995 | Ferrante et al. | |
| 5,454,816 A * | 10/1995 | Ashby | 606/88 |
| 5,462,550 A | 10/1995 | Dietz et al. | |
| 5,496,324 A | 3/1996 | Barnes | |

(Continued)

FOREIGN PATENT DOCUMENTS
DE    20303643    7/2003

OTHER PUBLICATIONS

European Search Report mailed Dec. 16, 2004 for European Application No. EP04256143, claiming benefit of U.S. Appl. No. 10/680,902 (now USPN 7,364,580).

*Primary Examiner* — Kevin T Truong
*Assistant Examiner* — Christopher Beccia
(74) *Attorney, Agent, or Firm* — Harness, Dickey

(57) ABSTRACT

A guide for cutting a bone comprising an anterior portion and a distal portion orientated at about a right angle to the anterior portion. The distal portion includes a guiding side, a distal surface at the guiding side, a box-cut shaped opening defined by the guiding side, a plurality of first cutting surfaces disposed at the guiding side at an acute angle relative to the distal surface of the guiding side operable to guide a cutting device to the bone to form chamfer cuts in the bone, and a second cutting surface disposed at the guiding side at least about a right angle to the distal surface operable to guide a cutting device to the bone to form a posterior cut in the bone.

15 Claims, 14 Drawing Sheets

U.S. PATENT DOCUMENTS

| | | |
|---|---|---|
| 5,591,207 A | 1/1997 | Coleman |
| 5,593,411 A * | 1/1997 | Stalcup et al. .................. 606/88 |
| 5,653,714 A | 8/1997 | Dietz et al. |
| 5,676,668 A | 10/1997 | McCue et al. |
| 5,769,854 A | 6/1998 | Bastian et al. |
| 5,810,829 A * | 9/1998 | Elliott et al. .................... 606/80 |
| 5,916,220 A * | 6/1999 | Masini ............................ 606/88 |
| 5,916,221 A | 6/1999 | Hodorek et al. |
| 5,925,049 A * | 7/1999 | Gustilo et al. .................. 606/82 |
| 5,935,132 A | 8/1999 | Bettuchi et al. |
| 5,957,925 A | 9/1999 | Cook et al. |
| 6,007,537 A * | 12/1999 | Burkinshaw et al. ........... 606/66 |
| 6,106,292 A | 8/2000 | Hollander et al. |
| 6,258,095 B1 * | 7/2001 | Lombardo et al. .............. 606/88 |
| 6,702,821 B2 | 3/2004 | Bonutti |
| 7,364,580 B2 * | 4/2008 | Cuckler et al. .................. 606/79 |
| 7,837,690 B2 * | 11/2010 | Metzger .......................... 606/87 |
| 8,016,833 B2 * | 9/2011 | Roger et al. .................... 606/88 |
| 2001/0001120 A1 | 5/2001 | Masini |
| 2002/0029045 A1 | 3/2002 | Bonutti |

* cited by examiner

US 8,246,626 B2

METHOD FOR PERFORMING BONE CUTTING

CROSS-REFERENCE TO RELATED APPLICATIONS

This application is a divisional of U.S. patent application Ser. No. 11/265,221 filed on Nov. 1, 2005, which is a continuation-in-part of U.S. patent application Ser. No. 10/680,902 filed on Oct. 8, 2003, now U.S. Pat. No. 7,364,580 issued on Apr. 29, 2008. The disclosure of the above application is incorporated herein by reference.

FIELD OF THE INVENTION

The present invention relates to a bone-cutting apparatus and associated method.

BACKGROUND OF THE INVENTION

Healthy knee joints include two cruciate ligaments, the anterior cruciate ligament (ACL) and the posterior cruciate ligament (PCL). The ACL is often damaged in diseased or injured knee joints, and may be removed during total knee replacement. It is considered desirable, however, to retain the PCL because of its importance for the stability of the knee during bending. When the PCL is damaged beyond repair or otherwise must be removed, a posterior stabilized knee prosthesis is implanted. This prosthesis includes a femoral component with an intercondylar box-shaped part. Therefore, a similarly box-shaped intercondylar bone portion must be resected from the femur to accommodate the femoral component.

Knee joints that require posterior stabilized knee prosthesis are typically severely damaged and intercondylar box resection is a challenging and painstaking procedure. Several cutting guides and milling devices have been developed to assist the surgeon in this procedure. Typically, two or more such guides, each designed to perform different resections, are needed to perform this procedure. The use of multiple guides increases the duration, complexity and cost of the procedure and is less than desirable. Therefore, there is a need for a single guide that can be used to perform multiple different resections.

SUMMARY OF THE INVENTION

In one form the invention provides for a guide for cutting a bone comprising an anterior portion and a distal portion orientated at about a right angle to the anterior portion. The distal portion includes a guiding side, a distal surface at the guiding side, a box-cut shaped opening defined by the guiding side, a plurality of first cutting surfaces disposed at the guiding side at an acute angle relative to the distal surface of the guiding side operable to guide a cutting device to the bone to form chamfer cuts in the bone, and a second cutting surface disposed at the guiding side at at least about a right angle to the distal surface operable to guide a cutting device to the bone to form a posterior cut in the bone.

In another form the invention includes a guide for cutting bone comprising an anterior portion, a posterior portion, a distal portion, a box-cut shaped opening, and a rotatable rod. The posterior portion is orientated at least approximately parallel to the anterior portion. The posterior portion includes a first posterior flange and a second posterior flange. A distal portion is orientated at least an approximate right angle to each of the anterior portion and the posterior portion. The distal portion includes a distal surface, a first guiding side, a second guiding side spaced apart from the first guiding side, and a plurality of cutting surfaces disposed at each of the first guiding side and the second guiding side at an acute angle relative to the distal surface of the first and second guiding sides operable to guide a cutting device to the bone to form chamfer cuts in the bone. The box-cut shaped opening is defined by the anterior portion, the first guiding side, the second guiding side, the first posterior flange, and the second posterior flange. The rotatable rod extends between the first posterior flange and the second posterior flange, the rotatable rod including a hole operable to receive and guide a cutting device for forming a box cut in the bone.

In yet another form, the present invention provides for a method for guiding a cutting device to a bone to form chamfer cuts, posterior cuts, and a box cut in the bone, the method includes: positioning a cutting guide on the bone such that an anterior portion of the cutting guide abuts an anterior bone surface and a distal portion of the cutting guide abuts a distal bone surface, the distal portion includes a first guiding side and a second guiding side defining a box-cut shaped opening; cutting chamfer cuts in the bone by directing the bone cutting device along each of a plurality of first cutting surfaces disposed at each of the first guiding side and the second guiding side, the first cutting surfaces disposed at an acute angle relative to a distal surface of the guide; and cutting posterior cuts in the bone by directing the bone cutting device along second cutting surfaces disposed at each of the first guiding side and the second guiding side, the second cutting surfaces disposed at about a right angle to the distal surface of the guide.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF VARIOUS EMBODIMENTS

The following description of various embodiments is merely exemplary in nature and is in no way intended to limit the invention, its application, or uses.

Figure 1:
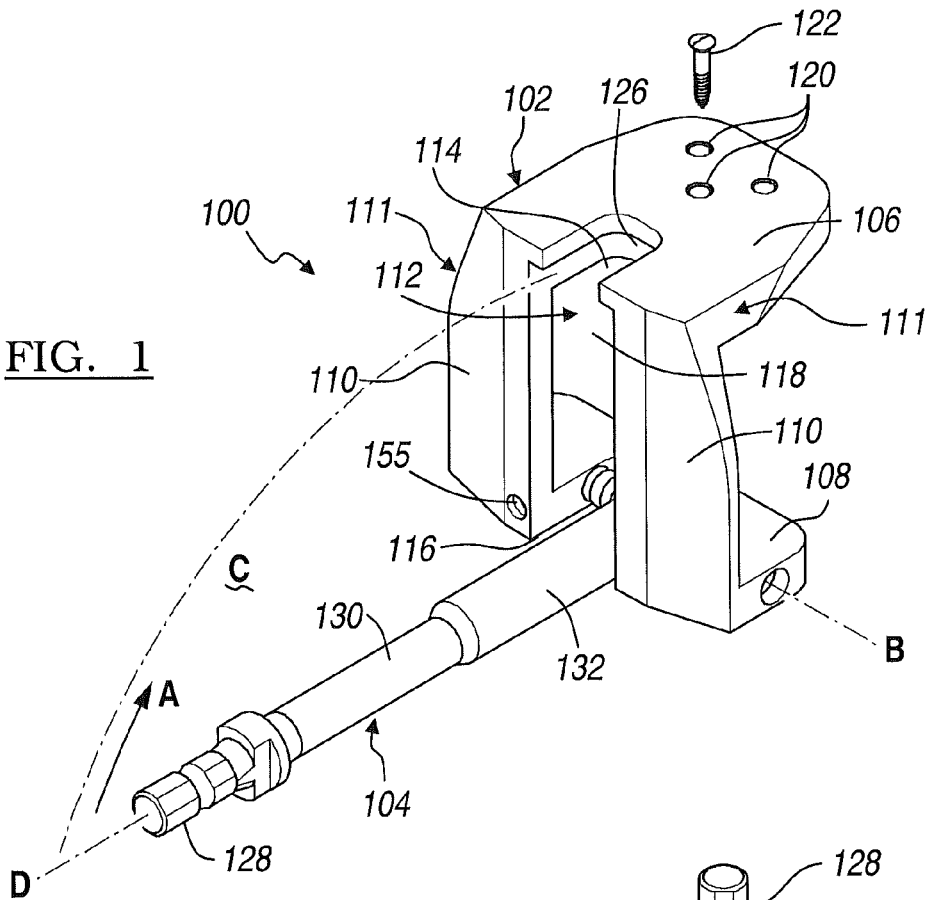
FIG. 1 is a perspective view of an embodiment of the bone cutting apparatus of the present invention, shown in a first position.

Referring to FIG. 1, an embodiment of a bone-cutting apparatus 100 according to the present invention is shown. The apparatus includes a guide 102 and a mill or reamer or similar cutting tool 104 that can rotate about its own longitudinal axis "D." The guide 102 may be a generally U-shaped member that includes a flange or anterior portion 106 and a base or posterior portion 108. The flange 106 and the base 108 are joined by a pair of guiding sides 110 at a distal portion 166, which are substantially orthogonal to the flange 106 and the base 108.

Figure 6:
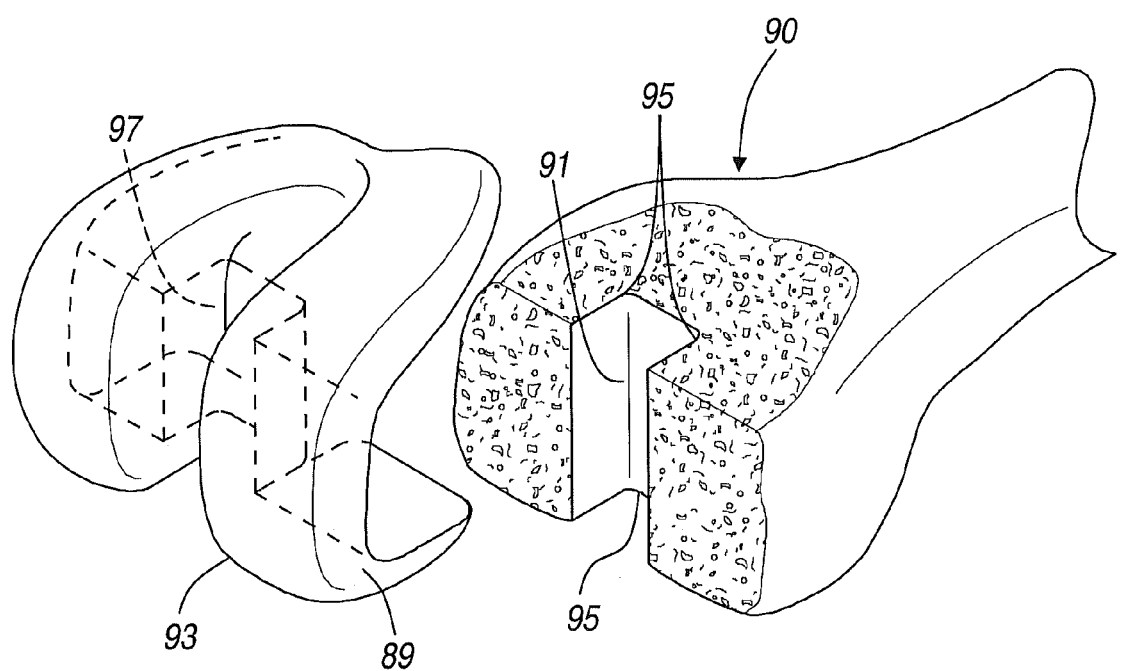
FIG. 6 is an exploded view of a portion of a distal femur prepared to receive a femoral component according to an embodiment of the present invention.

The guide 102 includes a generally "box-cut" shaped opening 112, which is defined by a U-shaped flange cutout 114, a U-shaped base cutout 116 and a rectangular spacing 118 between the guiding sides 110. The box-cut opening 112 is substantially sized and shaped to conform to the amount of bone that must be removed from a bone before inserting a portion of a prosthesis component. For example, in a posterior stabilized knee prosthesis, the opening 112 is sized for the removal of intercondylar bone which is necessary for the insertion of an intercondylar box 97 of the prosthesis (FIG. 6). In the following description, the bone-cutting apparatus 100, is described in reference to posterior stabilized knee prosthesis for the sake of clarity, but it should be appreciated that the apparatus 100, as well as the other bone cutting apparatuses described herein, is not restricted to such use.

Figure 4:
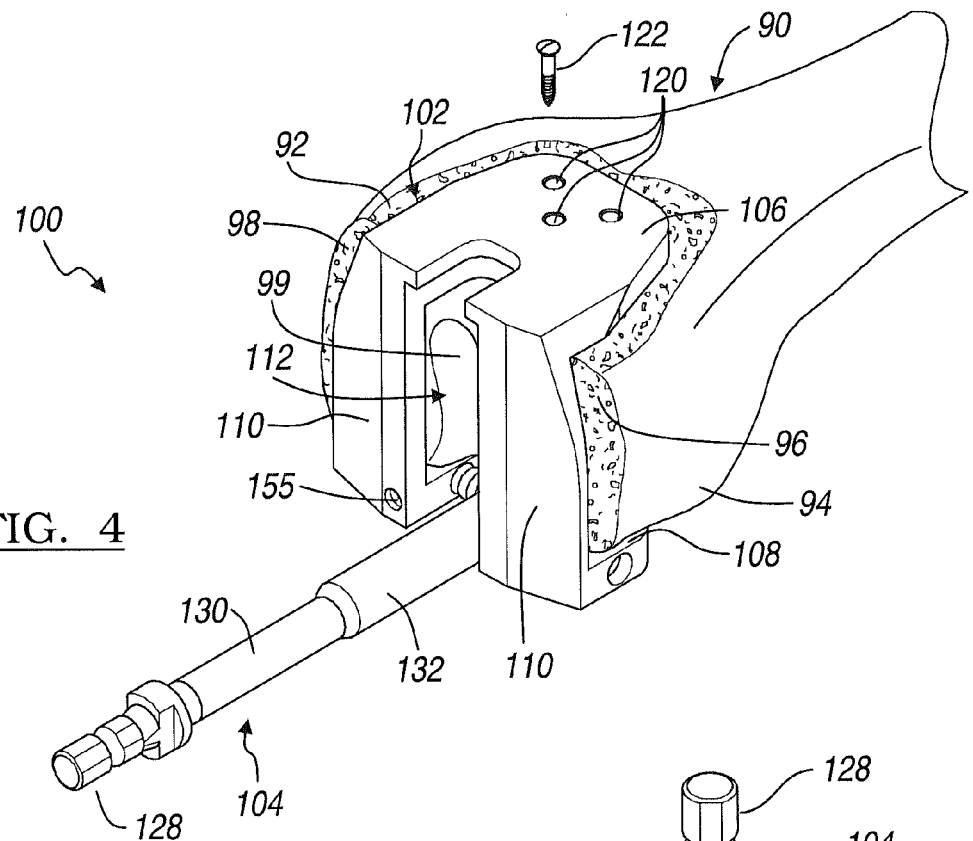
FIG. 4 is an environmental view of the embodiment of FIG. 1.

The flange 106 may include a plurality of holes 120 for securing the apparatus 100 to a bone using suitable removable fasteners 122, such as bone nails, drill bits, pins, etc. In a posterior stabilized knee prosthesis, for example, the apparatus 100 is used on the resected distal femur 90, as shown in FIG. 4. The flange 106 is placed on the resected anterior surface 92 and secured thereon with the fasteners 122. The base 108 is placed under the resected posterior surface 94, such that the guiding sides 110 are in front of the resected medial and lateral condyles 96, 98, shown for a right knee in FIG. 4. In this position, the opening 112 of the guide 102 may be aligned to remove an intercondylar bone portion 99.

Figure 2:
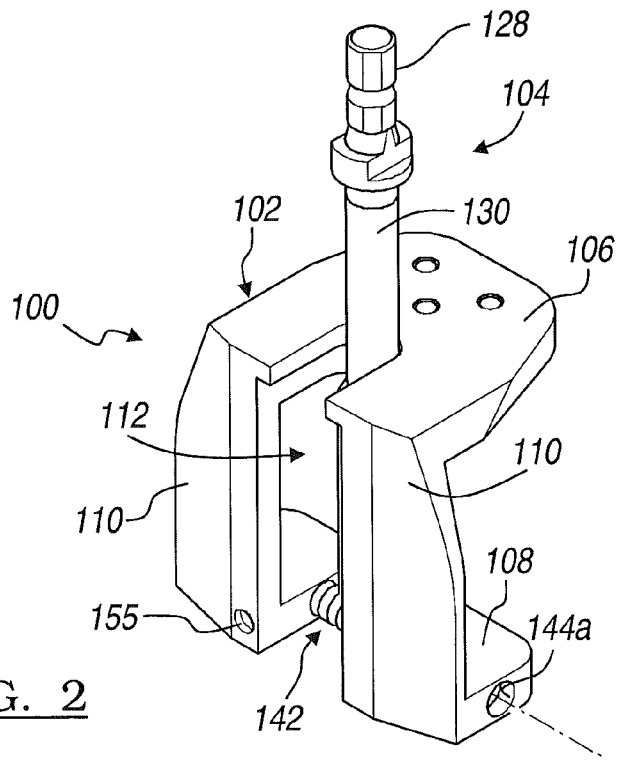
FIG. 2 is a perspective view of an embodiment of the bone cutting apparatus of the present invention, shown in a second position and a first lateral location.

The mill 104 is pivotably connected to the guide 102, such that it can rotate in the direction of an arrow "A" toward the flange 106 from a first position, shown in FIG. 1 to a last position shown in FIG. 2, and any position intermediate the first and the last positions. The term "second position" as used herein includes the last position and all the positions that span the interval between the first position and the last position in the direction of the arrow A.

In the first position, the mill 104 is substantially coplanar or parallel to the base 108 and it can move laterally along a lateral axis "B." In the last position, the mill 104 is prevented from rotating further in the direction of the arrow A by a stopping wall 126 of the flange cutout 114.

For a posterior stabilized knee prosthesis, the mill 104 is adjacent to the posterior surface 94 in the first position, and adjacent to the anterior surface 92 in the last position. The angle between the first and last positions is substantially 90° for a posterior stabilized knee prosthesis, but other angles less or greater than 90° may be provided by changing the depth of the flange cutout 114 or the angle of the guiding sides 110 with the flange 106 for other applications that do not require resection of rectangular bone portions.

Figure 5:
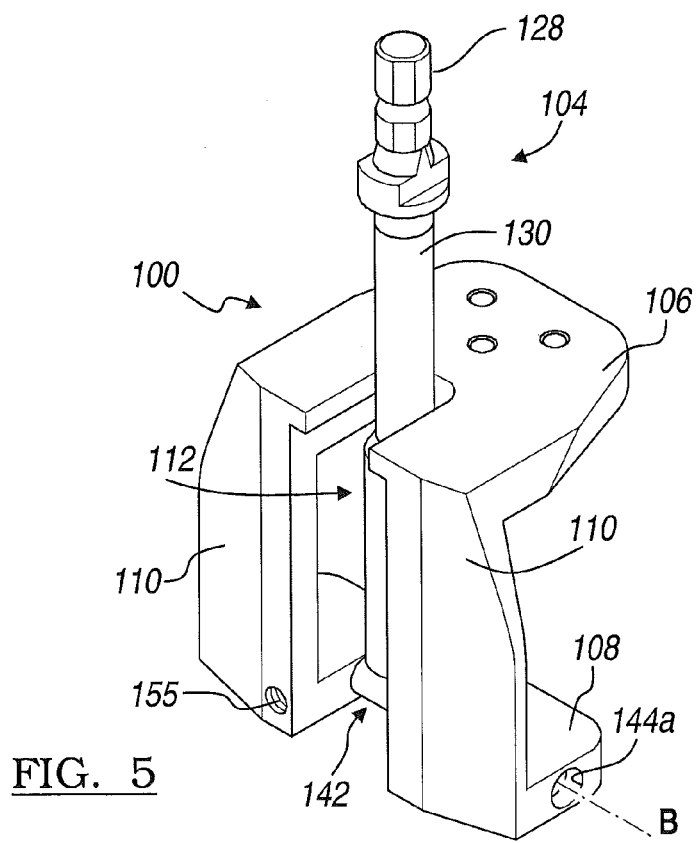
FIG. 5 is the embodiment of FIG. 2, shown in a second position and a second lateral location.

Referring to FIG. 5, the mill 104 includes a driven end 128, which may be connected to a spindle for power driven rotation or to a crank handle for manual rotation, and a shaft 130 with a cutting portion 132. The cutting portion 132 includes a bore 134 which rotatably receives a pivot pin 136. The pivot pin 136 has a threaded end 138 that engages a center receptacle that can take the form of a slot 140 in a cutting device receiver, which can take the form of a rod 142. The rod 142 is sized to be received in two halves 144a, 144b of a split bore 144 in the base 108, and is oriented coaxially with the lateral axis B. The rod 142 may be moved along the lateral axis B to allow lateral repositioning of the mill 104 relative to the box-cut opening 112.

In one embodiment, the rod 142 slides within the bore 144, such that the mill 104 is easily repositioned by manually shifting the shaft 130 laterally, i.e. in a direction parallel to the lateral axis B, thereby causing the rod 142 to slide within the bore 144. It will be appreciated that in some other applications, it may be desirable to control the lateral movement of the mill 104 by controlling the movement of the rod 142, such as, for example, by providing for threaded engagement between a portion of the rod 142 and a portion of the bore 144 and advancing the rod 142 using a tool such as a screwdriver or socket at one end of the rod 142, or other means within the purview of an artisan of ordinary skill.

In one embodiment, to better stabilize the mill 104 during cutting, lateral movement and repositioning of mill 104 is only permitted when the mill 104 is in the first position, in which no cutting occurs. When the mill 104 is pivoted toward the flange 106, lateral movement of the mill 104 may be prevented by preventing lateral movement of the rod 142. Thus, during pivoting, the mill 104 may be constrained to remain on a single cutting plane "C", i.e. on a plane that is perpendicular to the lateral axis B. Such lateral constraint may not be necessary for certain applications.

In one embodiment, the rod 142 may include one or more grooves 148 located at predetermined intervals along a first portion 143 of the rod 142. The grooves 148 are positioned such that one of them can selectively capture a pin 150 when the mill 104 is pivoted in the direction of the arrow A. The pin 150 is attached substantially perpendicularly to the base 108 and traverses the first half 144a of the bore 144. When the pin 150 is captured by one of the grooves 148, it prevents any lateral movement of the rod 142, thus stabilizing the lateral position of the mill 104 during cutting. The grooves 148 are truncated, i.e. they do not extend over the entire circumference of the rod 142, terminating at a chamfered portion 146 of the rod 142, which is oriented relative to the center slot 140 such that the pin 150 is not captured by any of the grooves 148, when the mill 104 is in the first position. When the mill 104 is pivoted about the lateral axis B, the rod 142 rotates about the same axis such that one of the grooves 148 captures the pin 150.

The rod 142 may include a set of detents 152 located on a second portion 145 of the rod 142. The first and second portions 143, 145 of the rod 142 are on opposite sides of the center slot 140 and are received within the respective halves 144a, 144b of the split bore 144. The detents 152 may extend over the entire circumference of the rod 142. A commercially available spring-loaded ball plunger 154 may be inserted in a hole 155 of the base 108 to selectively engage one of the detents 152. The detents 152 are placed at locations symmetric to the locations of the grooves 148 about the center slot 140, such that a desired lateral location for the mill 104 may be easily selected by moving the mill 104 laterally, while in the first position, until the ball 160 of the ball plunger 154 snaps into the appropriate detent 152. The ball plunger 154 and the detents 152, in cooperation with the grooves 148 and the pin 150, define an indexing mechanism 162 for quick lateral positioning and repositioning of the mill 104.

In one embodiment, there are three grooves 148 corresponding to three lateral locations of the mill 104 in relation to the opening 112, such that operation of the mill 104 in each lateral location removes one third (⅓) of the intercondylar bone 99. Two of these lateral locations are illustrated in FIGS. 2 and 5, in which the mill 104 has been pivoted to the last position. Depending on the quality/strength characteristics of the bone and the size of the bone 90 in the lateral dimension, i.e. the dimension along the lateral axis B and the size of the cutting portion 132 of the mill 104, a smaller or greater number of grooves 148 may be used. For fragile or damaged bone, for example, it may be desirable to use a greater number of smaller width cuts, in which case the rod 142 is provided with greater number of grooves 148 delineating a corresponding number of lateral locations.

Similarly, it will be appreciated that the number of lateral shifts of the mill 104 that are required for the removal of the bone portion 99 depends on the width of the bone portion 99 relative to the diameter of the cutting portion 132 of the mill 104. Therefore, it is also possible to remove the entire bone portion 99 with single pass of the mill 104, that is without need for any lateral shifting, if the diameter of the mill 104 substantially conforms to the size of the bone portion 99.

After the bone portion 99 is removed, a box-like cavity 91 with rounded corners 95 is defined in the bone 90 for receiving a femoral component 93, as shown in FIG. 6. When a small-diameter mill 104 is used, the corners 95 of the cavity 91 will have a smaller radius as compared to when a bigger diameter mill 104 is used. If right-angle corners are desired in a particular application, the surgeon could chisel the corners 95 of the cavity 91 to form right-angle corners 95. The guide 102 has two lateral surfaces 111, which are shaped similarly to corresponding lateral sides 89 of the femoral component 93 to aid in positioning the guide 102.

In operation, the bone-cutting apparatus 100 is attached to the resected bone 90 by inserting the bone 90 between the flange 106 and the base 108, such that the volume of the bone portion 99 to be removed is framed by the box-cut opening 112 of the apparatus 100. The apparatus 100 is then secured by attaching the flange 106 to the bone 90 with fasteners 122. Starting from the first position, the mill 104 is moved along the lateral axis B to a first lateral location while at the first position. The mill 104 is then rotated (spun) manually or by power, and is also pivoted from the first position to a second position, while remaining locked in the first lateral location and cutting through a segment of bone portion 99. Next, the mill 104 is returned to the first position and is shifted to a second lateral location along the lateral axis B, while in the first position. The shifting, pivoting and cutting process is repeated as necessary until the entire bone portion 99 is removed. During this procedure, selecting each of the lateral locations, i.e. moving the mill 104 from one to another cutting plane C, may be facilitated by the indexing mechanism 162.

Figure 7:
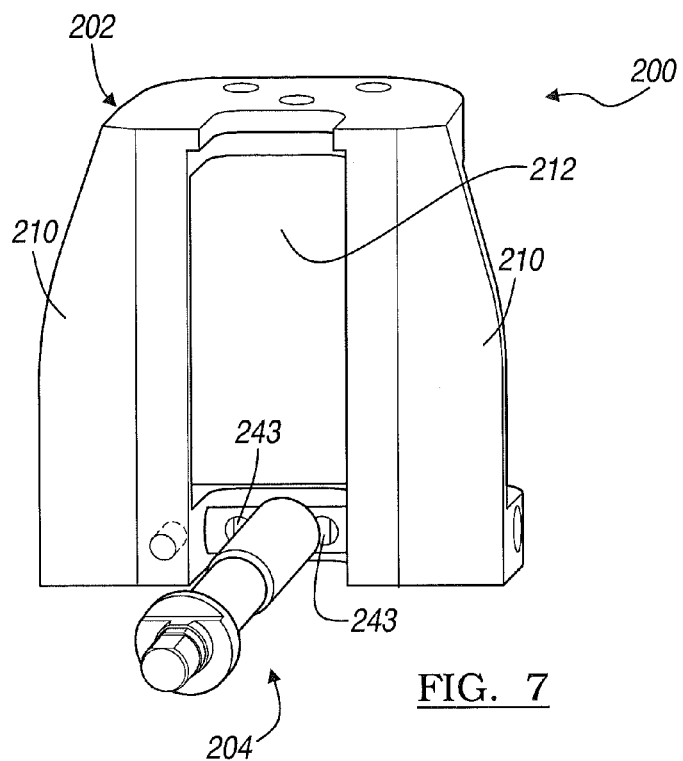
FIG. 7 is a perspective view of an embodiment of the bone cutting apparatus of the present invention, shown in a first position.
Figure 8:
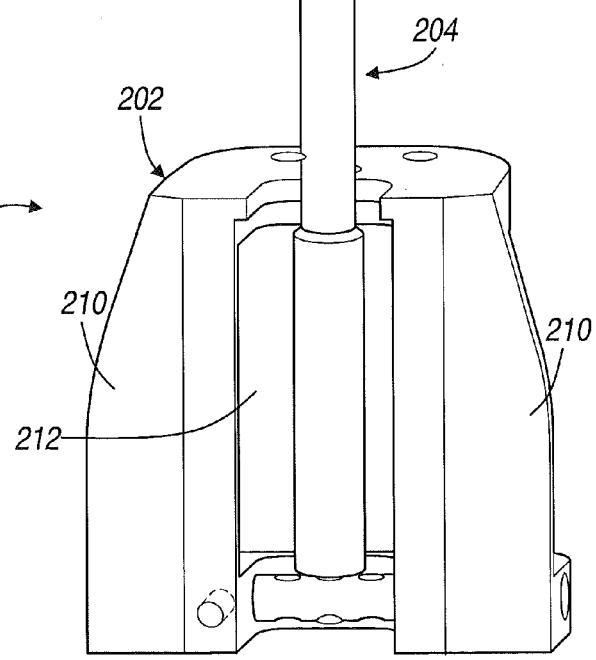
FIG. 8 is a perspective view of the bone cutting apparatus of FIG. 7, shown in a second position.
Figure 9:
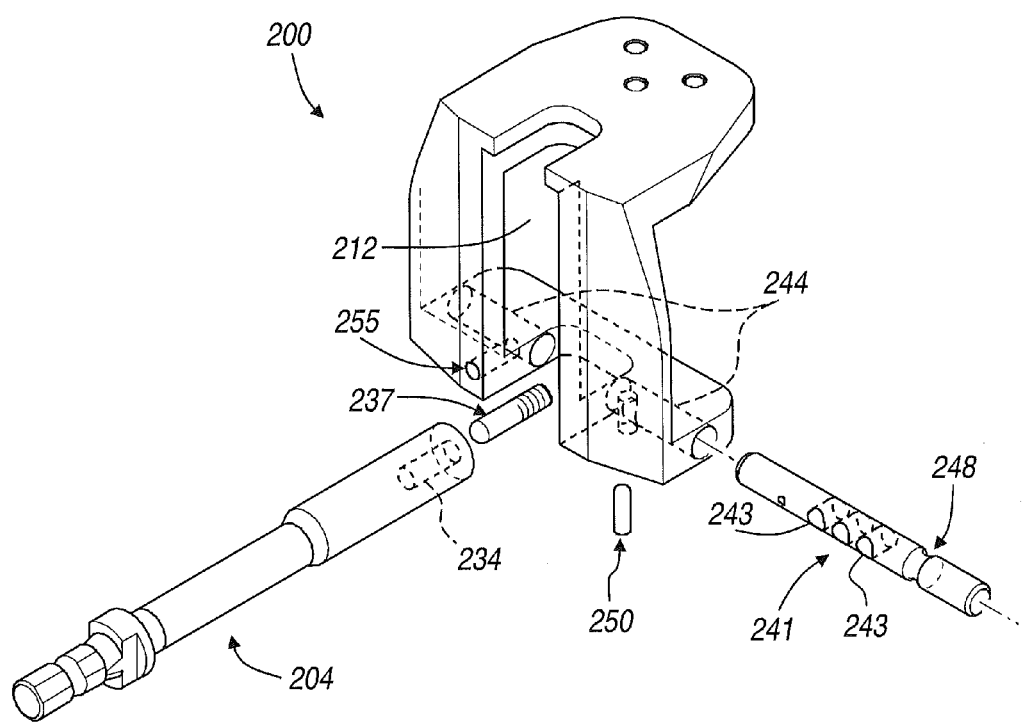
FIG. 9 is an exploded view of the bone cutting apparatus of FIG. 7.
Figure 10A:
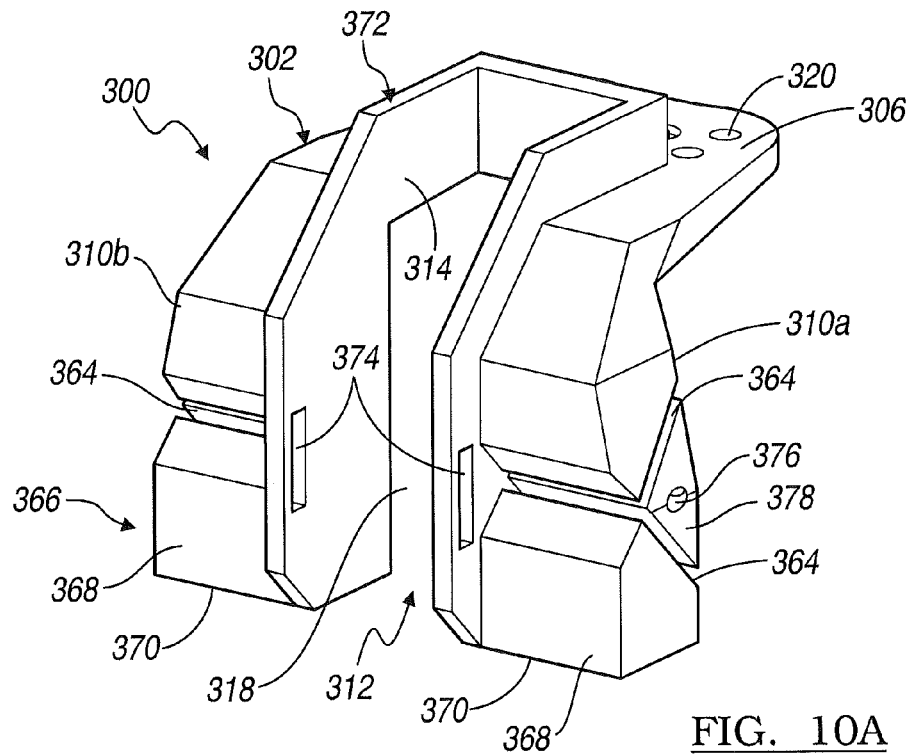
FIG. 10A is a first perspective view of another embodiment of the bone cutting device of the present invention.
Figure 10B:
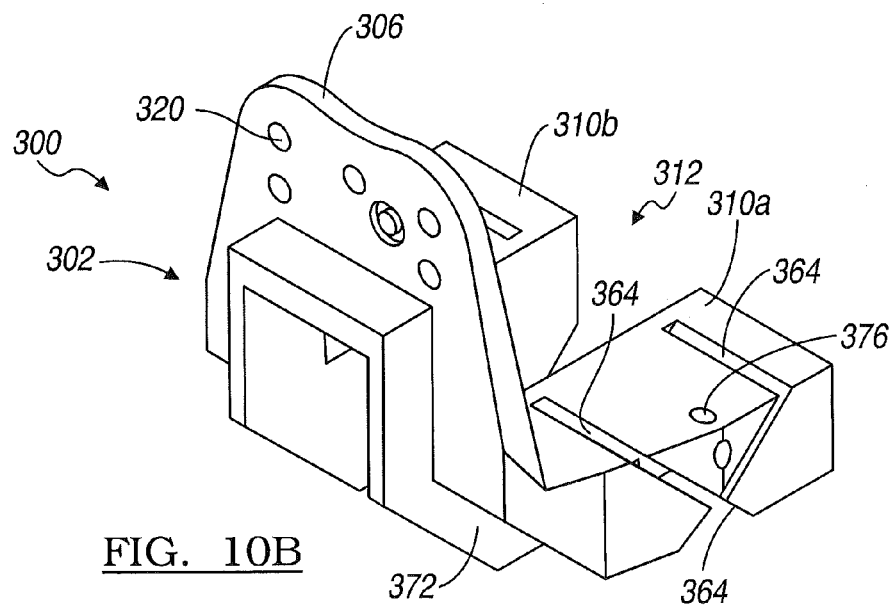
FIG. 10B is a second perspective view of the bone cutting device of FIG. 10A.
Figure 10C:
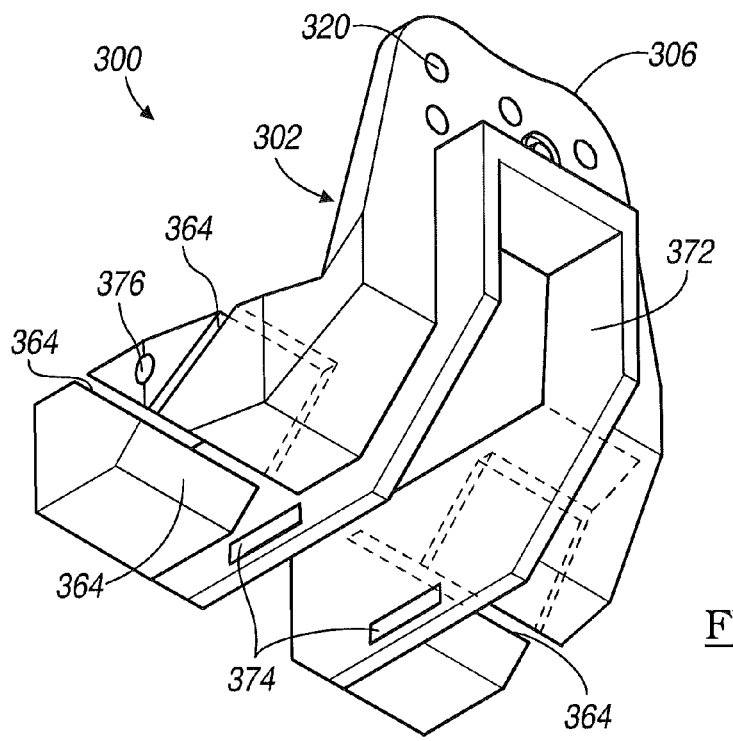
FIG. 10C is a third perspective view of the bone cutting device of FIG. 10A.
Figure 10D:
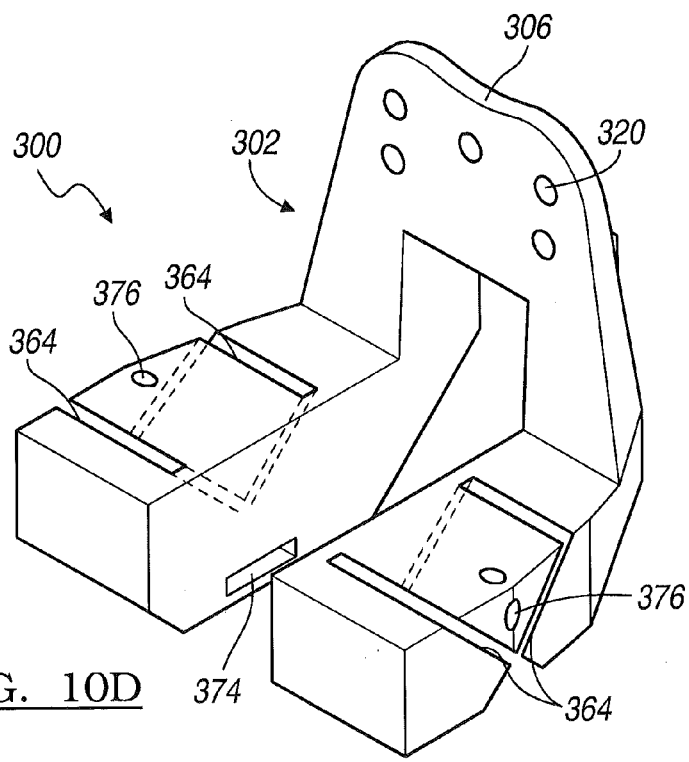
FIG. 10D is a fourth perspective view of the bone cutting device of FIG. 10A.
Figure 11A:
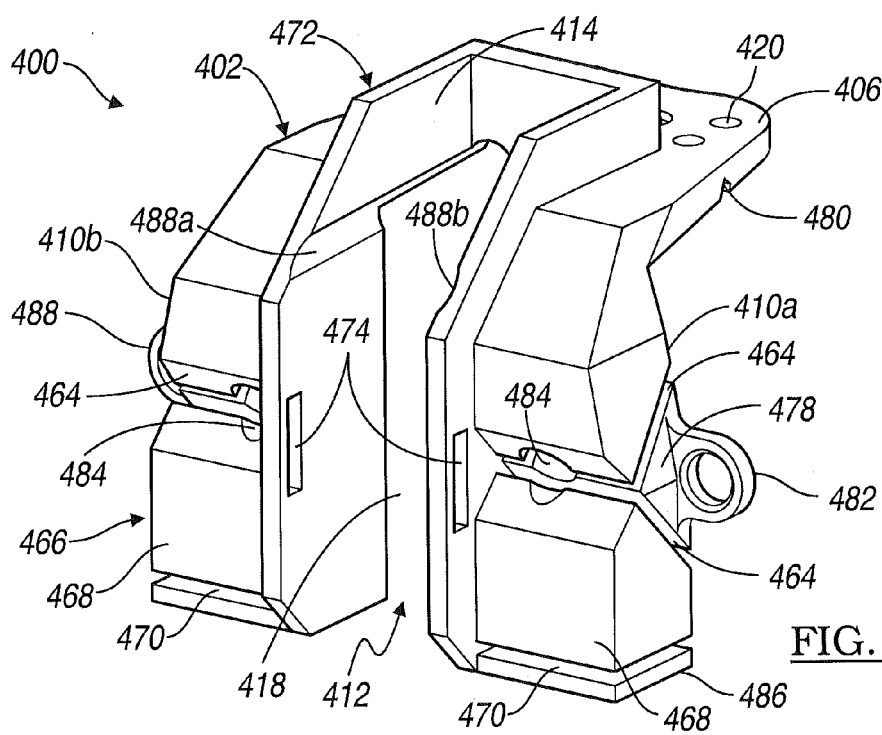
FIG. 11A is a first perspective view of a bone cutting device according to an additional embodiment of the present invention.
Figure 11B:
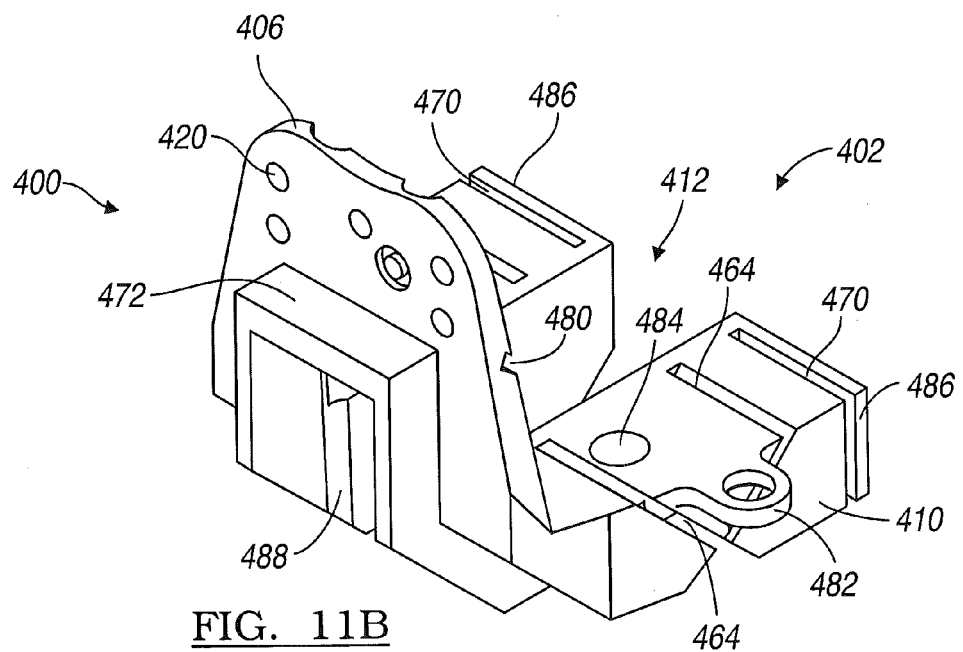
FIG. 11B is a second perspective view of the bone cutting device of FIG. 11A.
Figure 11C:
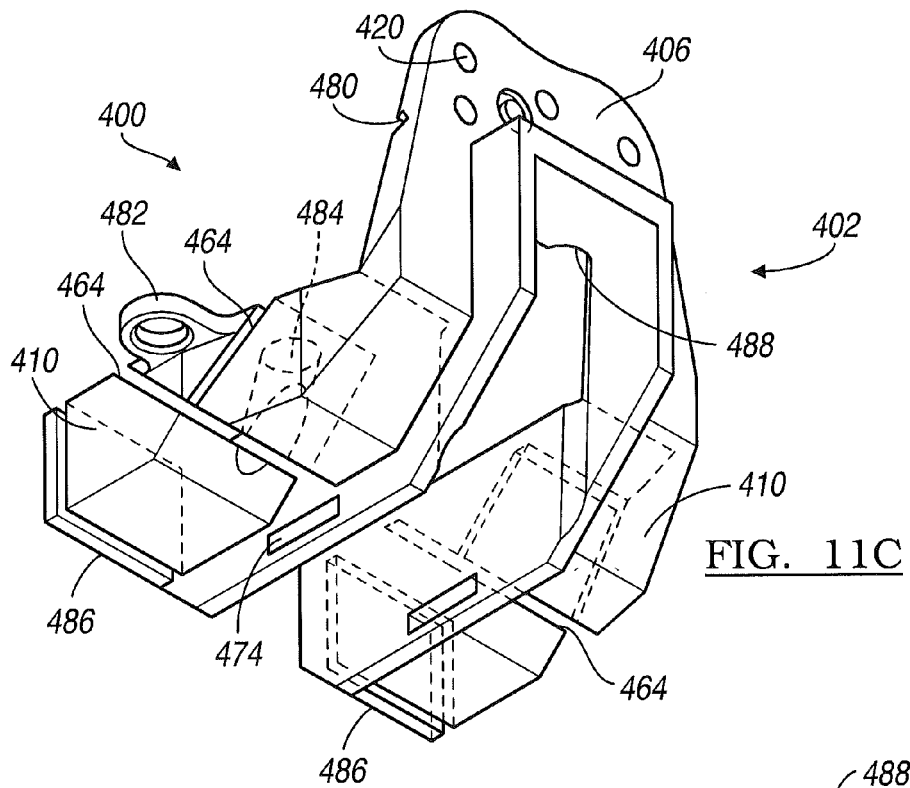
FIG. 11C is a third perspective view of the bone cutting device of FIG. 11A.
Figure 11D:
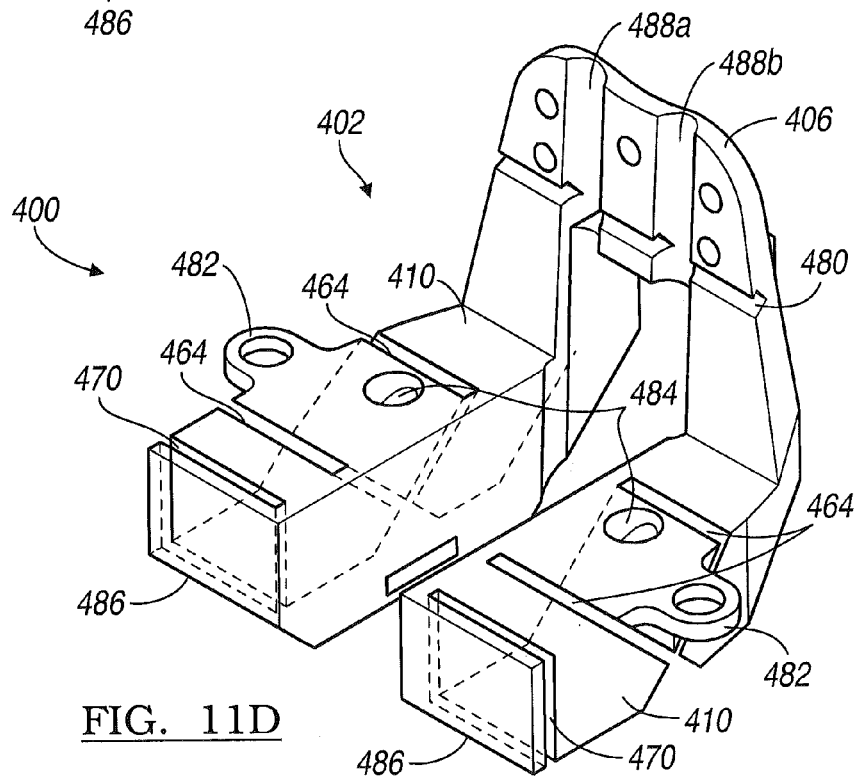
FIG. 11D is a fourth perspective view of a bone cutting device of FIG. 11A.
Figure 12A:
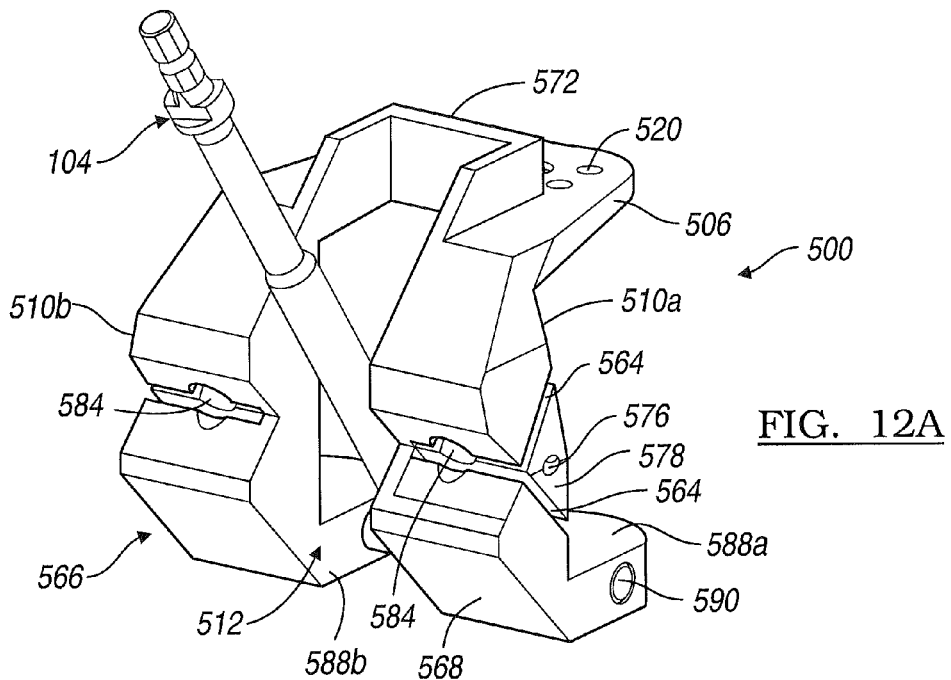
FIG. 12A is a first perspective view of a bone cutting device according to a further embodiment of the present invention.
Figure 12B:
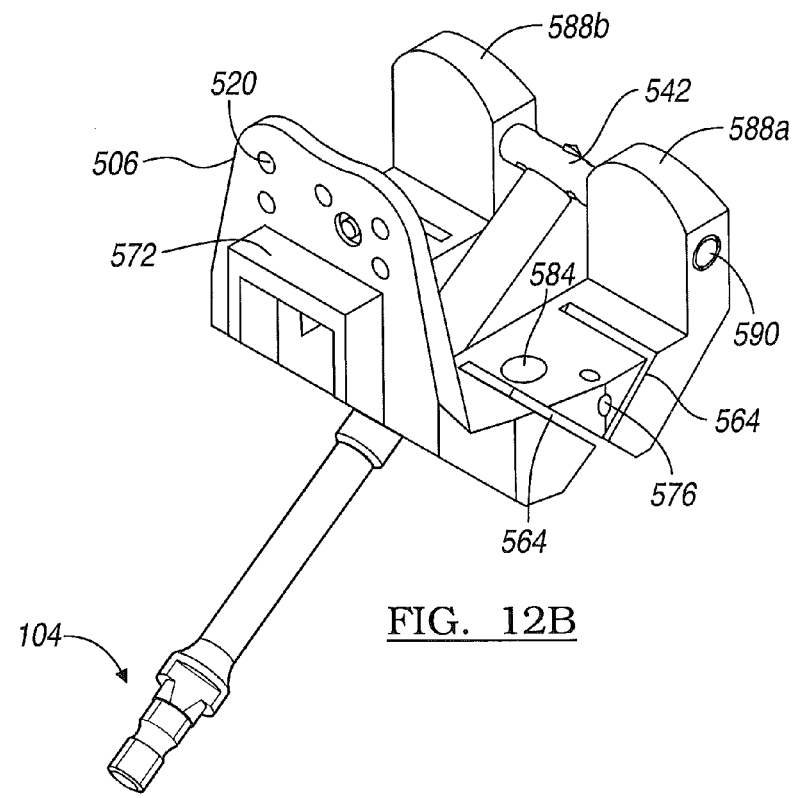
FIG. 12B is a second perspective view of a bone cutting device of FIG. 12A.
Figure 12C:
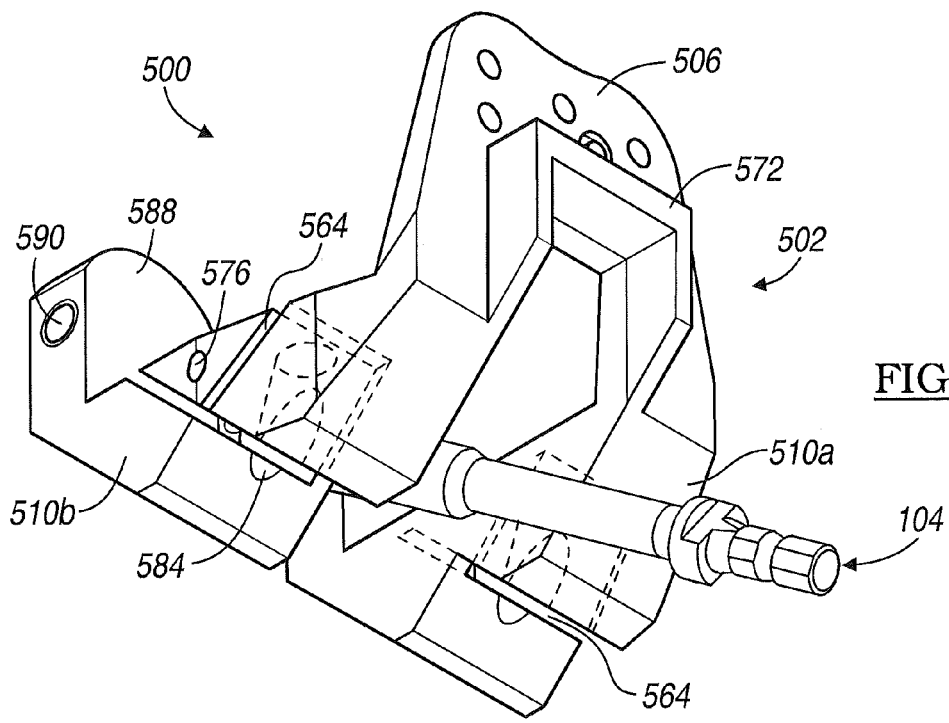
FIG. 12C is a third perspective view of a bone cutting device of FIG. 12A.
Figure 12D:
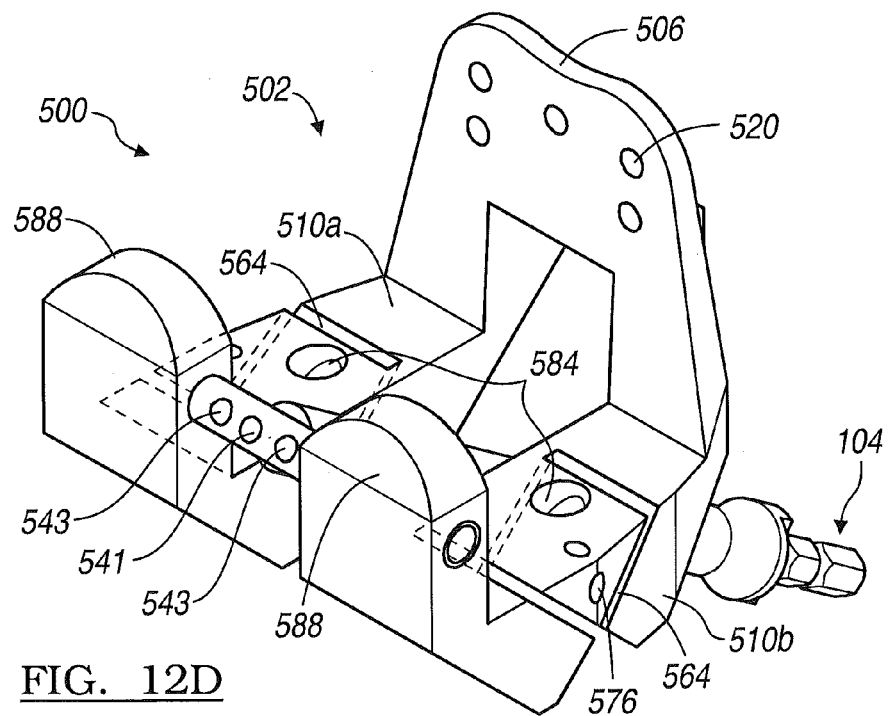
FIG. 12D is a fourth perspective view of a bone cutting device of FIG. 12A.

Another embodiment of the bone cutting apparatus 200 is illustrated in FIGS. 7-9. Elements common to embodiments 100 and 200 are referenced with numerals having the same second and third digits and prefaced by the digit 1 or 2 respectively, such as for example, the mill 104, 204. The description of elements common to both embodiments will not be repeated. In this embodiment, the rod 242 includes one groove 248 that captures the pin 250 to prevent lateral movement of the rod 242. The rod 242 includes a center hole 241 and two side holes 243, corresponding to the medial and lateral positions. To make a cut in the lateral or medial position, the mill 204 is removed from the center hole 241 of the rod 242 and is inserted in one of the side holes 243. To facilitate the engagement and disengagement of the mill 204 to and from the rod 142, the mill 204 includes a press-fit guide pin 237 which snaps inside one of the three holes 241, 243 and rotates with the mill 204.

A bone cutting apparatus according to an additional embodiment is illustrated in FIG. 10 at reference numeral 300. Elements common to embodiments 100 and 200 are referenced with numerals having the same second and third digits and prefaced by the digit 3. The above description of the like elements also applies to the apparatus 300.

The guide 302 further includes a plurality of first cutting surfaces 364. The cutting surfaces 364 extend through each of the first guiding side 310a and the second guiding side 310b, which generally form a distal portion 366 of the guide 302. As illustrated, each of the guiding sides 310 include two cutting surfaces 364. However, each guiding side 310 can include any suitable number of the first cutting surfaces 364 depending on the particular application.

The first cutting surfaces 364 are typically orientated at an acute angle relative to a distal surface 368 of the guiding sides 310. The distal surface 368 is the surface of the distal portion 366 opposite the side of the distal portion that abuts a bone that the guide 302 is mounted to during use, such as a bone 600 of FIG. 14. The first cutting surfaces 364 of each guiding side 310a can intersect each other, such as in the embodiment illustrated in FIG. 10, or the cutting surfaces 364 can be independent of each other. The first cutting surfaces 364 are generally planar and are operable to guide any suitable cutting device to the bone to be cut, such as a human femoral bone 600 of FIG. 14. The first cutting surfaces 364 can be used to make a number of cuts in the bone 600, such as chamfer cuts as described below. The second cutting surfaces can be incorporated into any of the other embodiments described herein.

The guide 302 includes second cutting surfaces 370. The second cutting surfaces 370 are disposed at the end or terminus of each of the first guiding side 310a and the second guiding side 310b. The second cutting surfaces 370 are generally planar and generally parallel to the anterior portion 306. The second cutting surfaces 370 can be used to direct a suitable cutting instrument to the bone to be cut, such as the human femoral bone 600 of FIG. 14. The second cutting surfaces 370 can be used to make a number of cuts in the bone 600, such as posterior cuts as described below.

Figure 14:
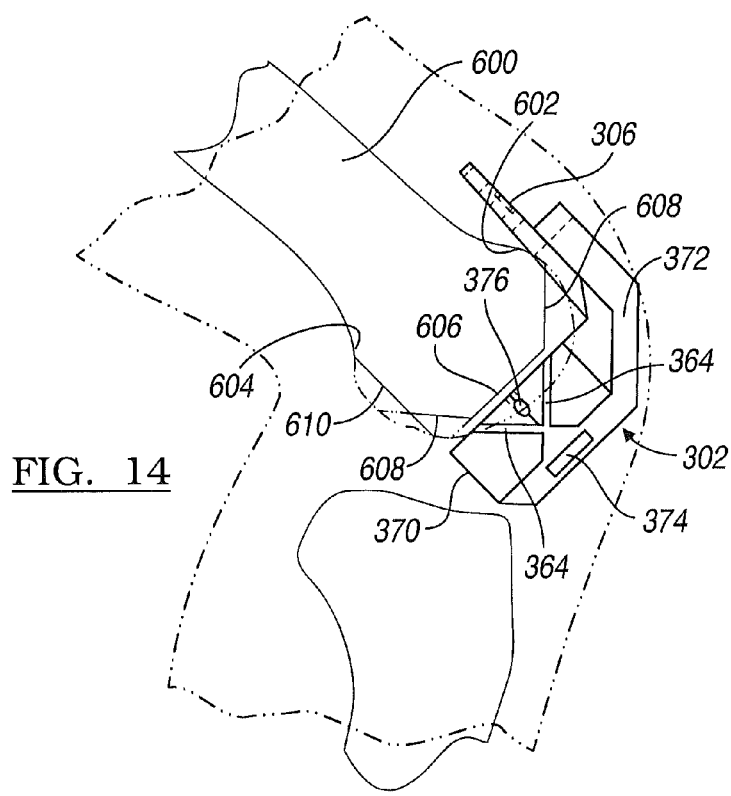
FIG. 14 is a side view of the bone cutting device of FIG. 10 mounted to a patient's femur.
Figure 15:
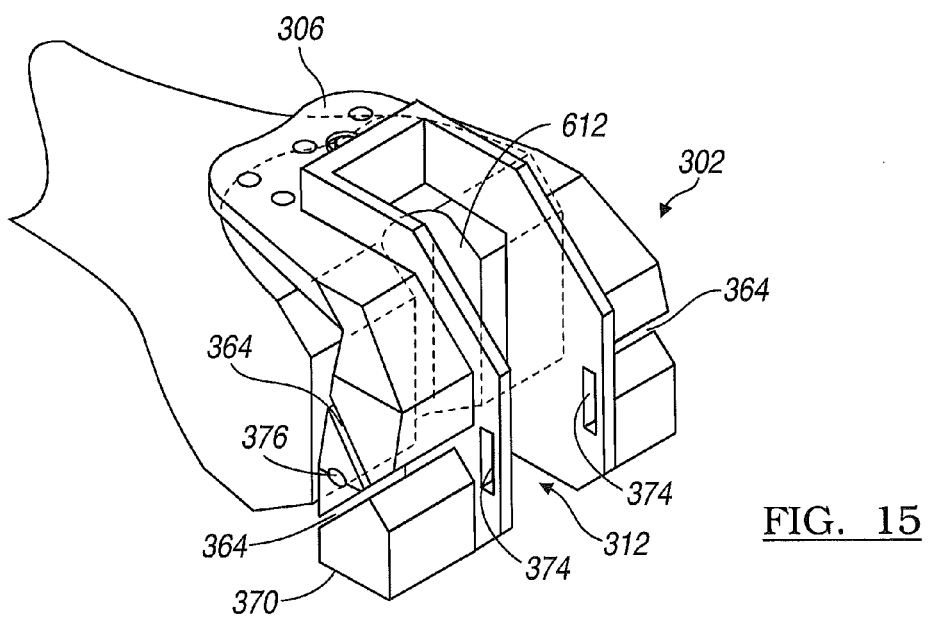
FIG. 15 is a perspective view of the bone cutting device of FIG. 10 mounted to a patient's femur.

A rim 372 further defines the box-cut shaped opening 312. The rim 372 extends along the portions of the guiding sides 310 and the anterior flange 306 that directly border and define the box-cut shaped opening 312. The rim 372 is raised from or extends from the rest of the guide 302. The rim 372 extends from the guide 302 in a direction opposite to the location of the bone that the guide 302 is attached to when it is in use, as illustrated in FIGS. 14 and 15. The rim 372 has a number of different functions. For example, the rim 372 serves as a guide or stop for the cutting device inserted through the box-cut opening 312 to form the box-cut in the bone 600.

The rim 372 can include one or more slits 374. The slits 374 can be located at a variety of different positions along the rim 372, such as proximate to the first cutting surfaces 364. The slits 374 can take a variety of different shapes and forms. For example, the slits 374 can be elongated or rectangular slits that extend lengthwise between the anterior flange 306 and the second cutting surface 370, as illustrated in FIG. 10. The slits 374 can also be in alignment with each other across the box-shaped opening 312. The slits 374 can be used for a variety of different purposes, such as to receive a removal device to assist in the removal of the guide 302 from the bone being cut.

An aperture 376 extends through each of the first guiding side 310a and the second guiding side 310b. The aperture 376 can take a variety of different forms and can be located at a variety of different locations on the guiding sides 310. For example, the aperture 376 can be located between the first cutting surfaces 364 and extend from an outside surface 378 of each of the guiding sides 310 to a surface of the guiding sides 310 that abuts the bone 600 when the guide 302 is in position on the bone 600. The apertures 376 can be used for a variety of different purposes, such as to receive a fastening device such as a pin or screw, to secure the guide 302 to the bone 600. The apertures 376 can be present in any of the other embodiments described herein.

An additional embodiment of the present invention is illustrated in FIG. 11 at reference numeral 400. Elements common to embodiments 100, 200, and 300 are referenced with numerals having the same second and third digits and prefaced by the digit 4. The above description of the like elements also applies to the apparatus 400.

The guide 402 includes a notch 480. The notch 480 is located in the anterior flange 406 on a side of the anterior flange 406 that abuts the bone 600 when the device is in its operable position about the bone 600 (FIGS. 14 and 15). As illustrated, the notch 480 is in alignment with one of the cutting surfaces 464 of each of the guiding sides 310a and 310b. The notch 480 can be used for a variety of different purposes, such as for a stop or guide for a cutting device inserted through the first cutting surfaces 464.

Extending from the outside surfaces 478 of each of the guiding sides 410 are securing flanges defining apertures 482. The apertures 482 are operable to receive any suitable fastening device capable of securing the guide 402 to the bone being cut with the guide 402. The apertures 482 can be incorporated into any other embodiment described herein. Further, the aperture 376 of the guide 302 can be incorporated into the guide 402.

The guide 402 can further include an aperture 484 that extends through one or both of the guiding sides 410. As illustrated, the aperture 484 is in the region of the first cutting surfaces 464 and extends through the first cutting surfaces 464 from the distal surface 468 completely through the distal portion 466. The aperture 484 is sized to receive any suitable fastening device capable for securing the guide 402 to bone. The aperture 484 can also be used to attach an augment trial. The aperture 484 can be included in any of the other embodiments described herein.

The second cutting surface 470 of the guide 402 is similar to the second cutting surface 370 of the guide 302. However, the second cutting surface 470 further comprises a posterior flange 486 that is spaced apart from the remainder of each of the guiding sides 410. Therefore, the second cutting surface 470 is not at the terminus of the guiding sides 410, but is between the flange 486 and the remainder of the guiding sides 410.

A first recess 488a and a second recess 488b are formed in the raised rim 472. The recesses 488 are positioned on opposing surfaces of the raised rim 472 in the region of the box-cut shaped opening 312. The recesses 488 are generally parallel to each other and in substantial vertical alignment with each other along the raised rim 472. The recesses 488 extend from the rim 472 to the flange 406. The recesses 488 are formed in a portion of the flange 406 that abuts the bone being cut when the guide is positioned at the bone. The recesses 488 can be of various shapes and sizes, but are generally semi-circular recesses.

The recesses 488 can have a variety of different functions. For example, the recesses 488 provide clearance in the corners of the box-cut shaped opening 312 for a cutting device to assist cutting the bone. The recesses 488 can be included in the other embodiments described herein.

A further embodiment of the present invention is illustrated in FIG. 12 at reference numeral 500. Elements common to embodiments 100, 200, 300, and 400 are referenced with numerals having the same second and third digits and prefaced by the digit 5. The above description of the like elements also applies to the apparatus 500.

The guide 502 includes a first posterior flange 588a and a second posterior flange 588b. The posterior flanges 588 extend from the distal portion 566 at an end opposite the anterior flange 506. The posterior flanges 588 are generally parallel to the anterior flange 506 and are generally perpendicular to the distal portion 566. The posterior flanges 588 can be separate as illustrated in FIG. 12 or can be unitary, such that the posterior flanges 588 take on a configuration similar to the base 108 of the guide 102.

The cutting device receiver or rod 542 extends between the posterior flanges 588. The rod 542 is seated within an opening 590 of each flange 588. The rod 542 can rotate within the openings 590 to any desirable degree depending upon the application. In some applications the rod 542 rotates approximately 90 degrees. The rod 542 includes the center hole 541 and can include, as illustrated, a plurality of the side holes 543. The center hole 541 and the side holes 543 receive the cutting tool 104, as described in the embodiments of guides 102 and 202.

Figure 3:
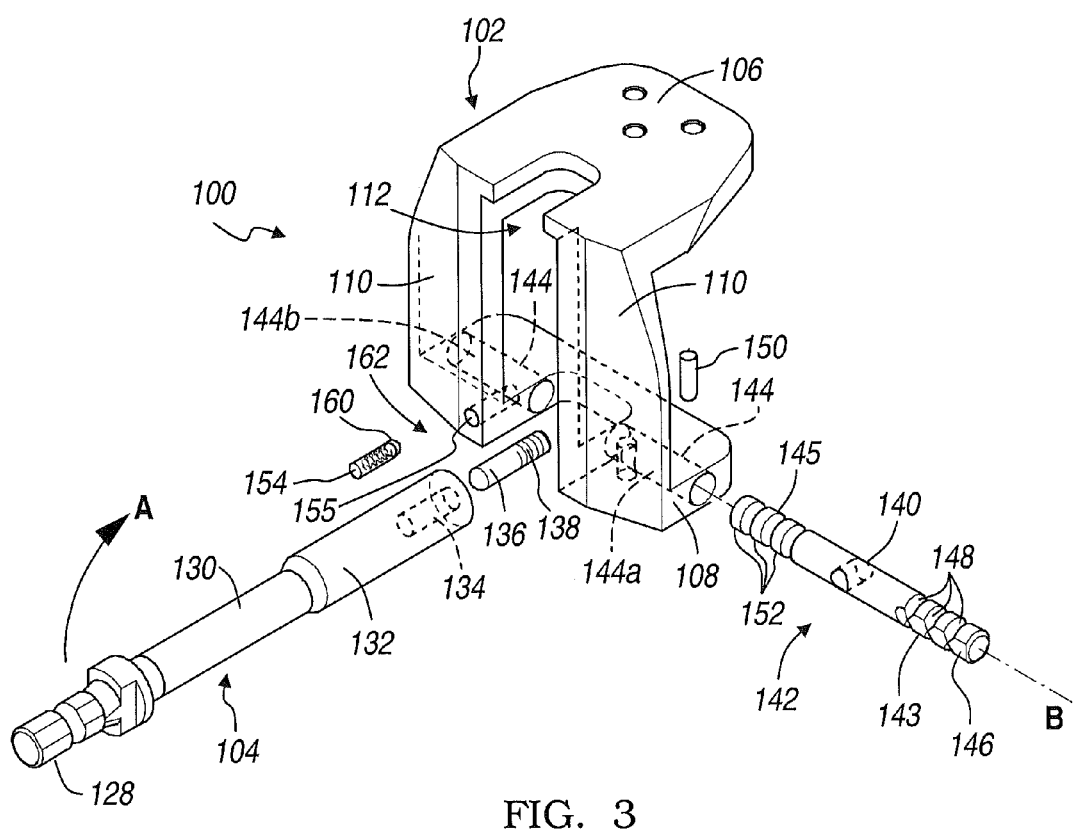
FIG. 3 is an exploded perspective view of an embodiment of the bone cutting apparatus of the present invention, shown in the first position.

The guide 502 can include any of the features of the other embodiments described herein, as would be understood by one of ordinary skill in the art. For example, the rod 542 can be replaced with the rod 142 of FIG. 3.

Figure 13:
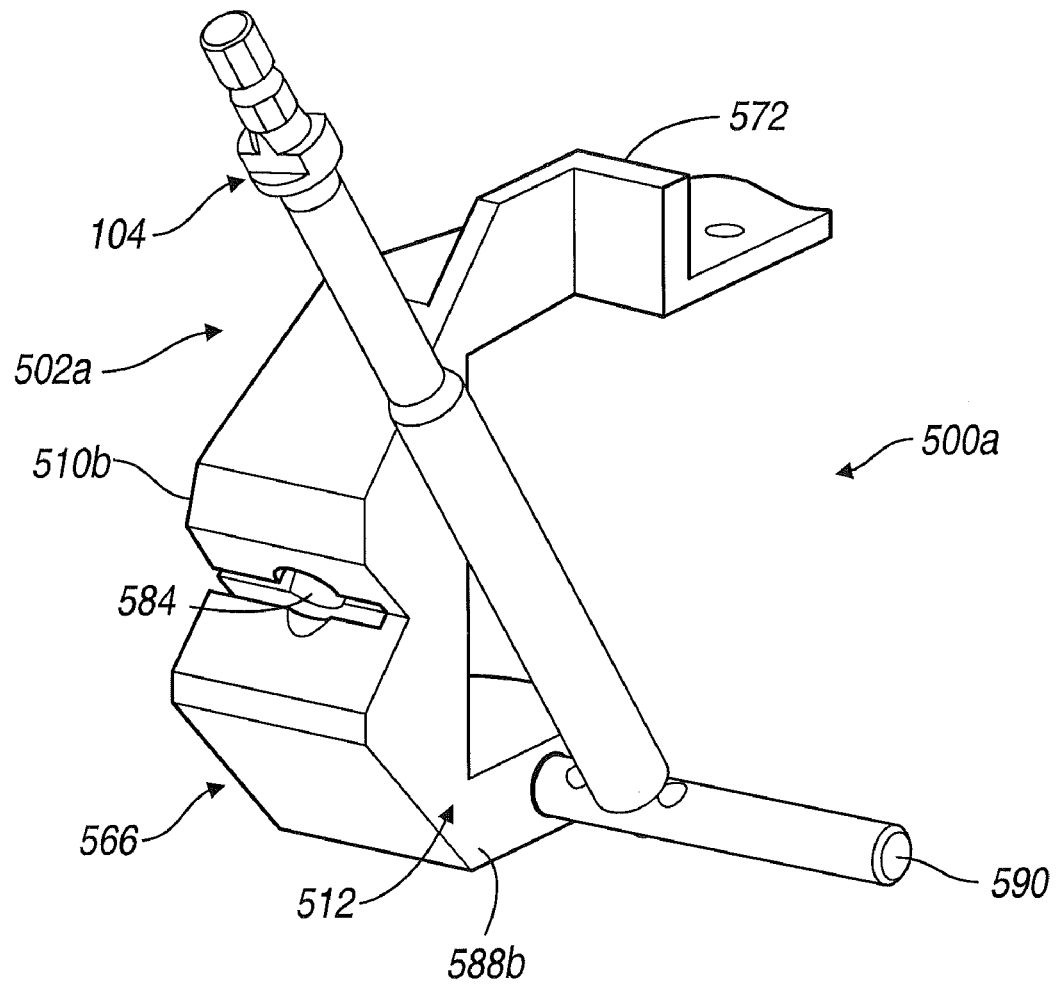
FIG. 13 is a perspective view of a bone cutting device according to a further embodiment of the present invention.

A further embodiment of the present invention is illustrated in FIG. 13 at reference numerals 500A and 502A. The guide 502A is substantially similar to the guide 502, except that the guide 502A does not include the guiding side 510a, the posterior flange 588a, or the portion of the anterior flange 506 associated with the guiding side 510a. Essentially, the guide 502A is one-half, the left half, of the guide 502 cut along its sagittal plane. Because the remainder of the guide 502A is substantially similar to the guide 502, elements common to both the guide 502 and the guide 502A are referenced with the same reference numbers. The description of the common elements provided above in conjunction with the description of the guide 502 also applies to the guide 502A. While the guide 502A is illustrated to include the left half of the guide 502, as cut along its sagittal plane, the orientation of the guide 502A can be reversed such that in some applications the guide includes the other half, or right half of the guide 502 as cut along its sagittal plane.

The guide 502A is suitable for use in a variety of different procedures, such as minimally invasive procedures. Any of the other devices 100, 200, 300, and 400 described herein can also be provided with a single guiding side 110, 210, 310, and 410 to make the devices 100, 200, 300, and 400 better suited for use in minimally invasive procedures.

With additional reference to FIGS. 14 and 15, use of the guide 302 to make resections in a human femoral bone 600 is illustrated. The bone 600 generally includes an anterior surface 602, a posterior surface 604, and a distal surface 606. The guide 302 is positioned at the bone 600 such that the anterior flange 306 is at the anterior surface 602 and the distal portion 366 is at the distal surface 606. The guide 302 is secured to the bone 600 in any suitable manner. For example, a suitable fastener can be inserted through the aperture 376, or the aperture 484 if included in the guide 302, to engage the bone 600 and secure the guide 302 to the bone.

With the guide 302 in position, chamfer cuts 608, a posterior cut 610, and a box cut 612 can be made. The cuts 608, 610, and 612 can be made in any order depending on the application. Further, not all of the cuts 608, 610, and 612 need be made.

The chamfer cuts 608 are made by directing a cutting device, such as a saw, knife, or other sharp edge, to the bone 600 through the first cutting surfaces 364. The position and orientation of the first cutting surfaces 364 properly aligns the knife at the bone 600 to form the chamfer cuts 608 at a desired position in the bone 600.

The posterior cut 610 is made by directing a cutting device, such as a knife or sharp edge, to the bone 600 using the second cutting surface 370. The knife is directed along the second cutting surface 370 to the posterior surface 604 of the bone 600. The position and orientation of the second cutting surface 370 properly aligns the knife at the bone to form the posterior cuts 610 at a desired position in the bone 600.

The box cut 612 is made by directing a suitable cutting device, such as a knife, punch, or the rotating mill 104 to the distal surface 606 of the bone 600. The cutting device is inserted within the box-cut shaped opening 312 and resects the portion of the bone 600 beyond the box-cut shaped opening 312. The cutting device is directed along the raised rim 372 to define the outer perimeter of the box cut 612.

After the cuts 608, 610, and 612 are made, the guide 302 is removed from the bone 600. The guide 302 can be removed from the bone 600 in any suitable manner, such as by inserting a removal device through the slits 374 and pulling the guide 302 from the bone.

After the guide 302 is removed, a suitable implant, such as the femoral component 93, can be secured to the bone. The procedure for securing the femoral component 93 is described above.

The procedures for making the cuts 608, 610, and 612 using the guides 402, 502, and 502A is substantially similar to the procedures described above with respect to the guides 102, 202, and 302.

With respect to the guide 502A, the guide 502A only overlaps a single condyle, the left condyle, of the femoral bone 600 to make the chamfer cuts 608 and the posterior cut 610 in the left condyle. In embodiments where it is desirable to make the chamfer cuts 608 and the posterior cut 610 in the right condyle, the guide 502A having the right guiding side 510a, as opposed to the left guiding side 510b, and the right posterior flange 588a, as opposed to the left posterior flange 588b, is used.

The various embodiments of the bone-cutting apparatuses described herein provide a convenient cutting tool, which can guide and resect a portion of a bone, such as an intercondylar box portion, for example, quickly and precisely. By providing a pivotable mill, which can also be selectively shifted in a lateral direction, the intercondylar box portion can be removed without the need to apply any impact forces. The bone-cutting apparatus described herein may be an important component of a knee replacement system that includes femoral components 93, such as those used for posterior stabilized knee prosthesis.

The bone-cutting apparatuses described herein also provide a convenient three-in-one tool for making the chamfer cuts 608, the posterior cuts 610, and the box cut 612. Use of the guides eliminates the need to use a separate device to make each of the cuts 608, 610, and 612. Therefore, the guides save operating time, save costs associated with purchasing additional equipment, and reduce the complexity of preparing a bone to receive an implant.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method for guiding a cutting device to a bone to form chamfer cuts, posterior cuts, and a box cut in the bone, the method comprising:
    positioning a cutting guide having a box-cut opening and a base on the bone;
    cutting chamfer cuts in the bone along each of a plurality of cutting surfaces disposed at an acute angle relative to a distal surface of the guide;
    moving a rotatable mill coupled to the guide along the base by removing the mill from a first hole of a rod rotatably supported on the base and coupling the mill to a second hole of the rod;
    pivoting the mill relative to the base within the box-cut opening of the guide;
    rotating the mill about a longitudinal axis of the mill while pivoting the mill; and
    cutting a box-cut in the bone using the mill.

2. The method of claim 1, further comprising:
    cutting posterior cuts along posterior cutting surfaces of the cutting guide.

3. The method of claim 1, further comprising engaging a pin attached to the guide into a groove of the rod while pivoting the mill.

4. The method of claim 1, further comprising preventing lateral movement of the mill while pivoting the mill.

5. A method for performing a box resection of a bone, the method comprising:
    attaching a bone-cutting apparatus to a bone, the bone cutting apparatus including a guide with a box-cut opening and a mill movably coupled to the guide and rotatable about a longitudinal axis of the mill;

moving the mill along a base of the box-cut guide and along a rod spanning the box-cut opening to a first lateral location;

rotating the mill about the longitudinal axis while pivoting the mill away from the base;

engaging a pin attached to the guide into a groove of the rod while pivoting the mill; and resecting the bone along a first lateral plane with the mill.

6. The method of claim 5, further comprising:

pivoting the mill toward the base;

moving the mill along the rod to a second lateral location;

rotating the mill about the longitudinal axis while pivoting the mill away from the base; and resecting the bone along a second lateral plane with the mill.

7. The method of claim 6, further comprising selecting the first and second lateral locations by using an indexing mechanism coupled to the rod.

8. The method of claim 6, further comprising selecting the first and second lateral locations by engaging a ball plunger to corresponding first and second detents on the rod, the ball plunger coupled to the base.

9. The method of claim 5, further comprising constraining movement of the mill along the rod while pivoting the mill.

10. The method of claim 5, further comprising cutting chamfer cuts in the bone along each of a plurality of cutting surfaces disposed at an acute angle relative to a distal surface of the guide.

11. The method of claim 5, further comprising cutting posterior cuts along posterior cutting surfaces of the cutting guide.

12. The method of claim 5, wherein the box-cut opening is defined by an anterior portion, a first guiding side, a second guiding side, a first posterior flange, and a second posterior flange of the guide.

13. The method of claim 12, wherein the guide includes a U-shaped raised rim that extends above the anterior portion of the box-cut opening.

14. The guide of claim 12, further comprising securing the guide to the bone through first and second apertures on the corresponding first and second guiding sides.

15. The guide of claim 12, wherein the first guiding side defines two cutting surfaces that intersect each other.

* * * * *

UNITED STATES PATENT AND TRADEMARK OFFICE
CERTIFICATE OF CORRECTION

| | | |
|---|---|---|
| PATENT NO. | : 8,246,626 B2 | Page 1 of 1 |
| APPLICATION NO. | : 12/719344 | |
| DATED | : August 21, 2012 | |
| INVENTOR(S) | : Cuckler et al. | |

It is certified that error appears in the above-identified patent and that said Letters Patent is hereby corrected as shown below:

Title Page, No. (57), Abstract, Line 9 insert --at-- before "at".

Signed and Sealed this
Twelfth Day of February, 2013

Teresa Stanek Rea
*Acting Director of the United States Patent and Trademark Office*